(12) United States Patent
Yang et al.

(10) Patent No.: US 9,890,093 B2
(45) Date of Patent: Feb. 13, 2018

(54) OLEFIN OLIGOMERIZATIONS USING CHEMICALLY-TREATED SOLID OXIDES

(71) Applicant: Chevron Phillips Chemical Company LP, The Woodlands, TX (US)

(72) Inventors: Qing Yang, Bartlesville, OK (US); Uriah J. Kilgore, Kingwood, TX (US); Max P. McDaniel, Bartlesville, OK (US); Brooke L. Small, Kingwood, TX (US); Kenneth D. Hope, Kingwood, TX (US); Eduardo J. Baralt, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/977,728

(22) Filed: Dec. 22, 2015

(65) Prior Publication Data

US 2017/0174584 A1    Jun. 22, 2017

(51) Int. Cl.
*C07C 2/10* (2006.01)
*C07C 9/15* (2006.01)

(52) U.S. Cl.
CPC ............ *C07C 2/10* (2013.01); *C07C 9/15* (2013.01); *C07C 2527/053* (2013.01); *C07C 2527/06* (2013.01)

(58) Field of Classification Search
CPC ... C07C 2/10; C07C 2527/06; C07C 2521/04; C07C 2521/08; C07C 2527/053; B01J 33/00; B01J 35/008; B01J 2231/20
USPC .......................... 585/16, 510, 515
See application file for complete search history.

(56) References Cited

U.S. PATENT DOCUMENTS

| | | | |
|---|---|---|---|
| 5,883,036 A | 3/1999 | Fujie et al. | |
| 6,107,230 A | 8/2000 | McDaniel et al. | |
| 6,165,929 A | 12/2000 | McDaniel et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 7,026,494 B1 * | 4/2006 | Yang | B01J 31/143 502/120 |
| 7,294,599 B2 | 11/2007 | Jensen et al. | |
| 7,601,665 B2 | 10/2009 | McDaniel et al. | |
| 7,884,163 B2 * | 2/2011 | McDaniel | C08F 10/02 502/103 |
| 7,897,539 B2 | 3/2011 | McDaniel | |
| 8,309,485 B2 | 11/2012 | Yang et al. | |
| 8,536,391 B2 * | 9/2013 | Small | C08F 10/14 585/254 |
| 8,623,973 B1 | 1/2014 | McDaniel et al. | |
| 8,703,886 B1 * | 4/2014 | Yang | C08F 110/02 502/119 |
| 9,023,959 B2 | 5/2015 | McDaniel et al. | |
| 2004/0068072 A1 * | 4/2004 | Small | C07C 11/02 526/348.2 |
| 2005/0288178 A1 | 12/2005 | Jensen et al. | |
| 2009/0062167 A1 * | 3/2009 | Kaneko | C09K 5/042 508/567 |
| 2010/0076167 A1 * | 3/2010 | McDaniel | C08F 10/02 526/130 |
| 2010/0317904 A1 * | 12/2010 | Small | C08F 10/14 585/18 |
| 2010/0322836 A1 | 12/2010 | Benham et al. | |
| 2011/0092357 A1 | 4/2011 | McDaniel et al. | |
| 2013/0217843 A1 * | 8/2013 | McDaniel | C08F 210/14 526/108 |
| 2014/0275664 A1 * | 9/2014 | Yang | C10G 50/00 585/18 |
| 2015/0203617 A1 | 7/2015 | McDaniel et al. | |

\* cited by examiner

*Primary Examiner* — In Suk Bullock
*Assistant Examiner* — Aaron Pierpont
(74) *Attorney, Agent, or Firm* — Merchant & Gould P.C.

(57) ABSTRACT

Oligomerization processes include the steps of introducing a monomer containing a $C_3$ to $C_{30}$ olefin and a chemically-treated solid oxide into a reaction zone, and oligomerizing the monomer to form an oligomer product in the reaction zone. Fluorided silica-coated alumina and fluorided-chlorided silica-coated alumina are illustrative chemically-treated solid oxides that can be used in the oligomerization processes.

17 Claims, No Drawings

OLEFIN OLIGOMERIZATIONS USING CHEMICALLY-TREATED SOLID OXIDES

BACKGROUND OF THE INVENTION

The present invention relates generally to processes for oligomerizing olefins using a chemically-treated solid oxide. In certain oligomerization processes, the chemically-treated solid oxide can comprise fluorided silica-coated alumina or fluorided-chlorided silica-coated alumina.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Processes for oligomerizing olefins are disclosed and described herein. Such processes can comprise (i) introducing a monomer comprising a $C_3$ to $C_{30}$ olefin and a chemically-treated solid oxide into a reaction zone, and (ii) oligomerizing the monomer to form an oligomer product in the reaction zone. In some embodiments, the monomer can comprise a $C_3$ to $C_{12}$ alpha olefin (or normal alpha olefin) and the chemically-treated solid oxide can comprise fluorided silica-coated alumina, fluorided-chlorided silica-coated alumina, or sulfated alumina. These processes can provide unexpectedly high olefin conversions and desirable selectivity to various oligomer product fractions (e.g., dimers or trimers).

Polyalphaolefins (PAO's) also are disclosed and described herein. In an embodiment of this invention, the PAO's can be characterized by a viscosity index greater than or equal to 110 and a kinematic viscosity at $-40°$ C. of less than or equal to 1750 cSt. The PAO's can comprise $C_{24}$ saturated hydrocarbons, or can comprise hydrogenated oligomers of a $C_6$ to $C_{12}$ olefin, but are not limited thereto.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, compositions, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

Regarding claim transitional terms or phrases, the transitional term "comprising," which is synonymous with "including," "containing," "having," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claimed invention. A "consisting essentially of" claim occupies a middle ground between closed claims that are written in a "consisting of" format and fully open claims that are drafted in a "comprising" format. Absent an indication to the contrary, describing a composition or method as "consisting essentially of" is not to be construed as "comprising," but is intended to describe the recited element that includes materials or steps which do not significantly alter the composition or method to which the term is applied. For example, a monomer consisting essentially of a material A can include impurities typically present in a commercially produced or commercially available sample of the recited compound or composition. When a claim includes different features and/or feature classes (for example, a method step, monomer features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a monomer consisting of specific components; alternatively, consisting essentially of specific components; or alternatively, comprising the specific components and other non-recited components. While compositions and methods are described in terms of "comprising" various components or steps, the compositions and methods can also "consist essentially of" or "consist of" the various components or steps, unless specifically stated otherwise. For example, a chemically-treated solid oxide consistent with certain embodiments of the present invention can comprise; alternatively, consist essentially of; or alternatively, consist of; a fluorided solid oxide.

The terms "a," "an," and "the" are intended to include plural alternatives, e.g., at least one, unless otherwise specified. For instance, the disclosure of "an electron-withdrawing anion" is meant to encompass one, or combinations of more than one, electron-withdrawing anion (e.g., sulfate, chloride, fluoride, etc.), unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

The terms "contact product," "contacting," and the like, are used herein to describe compositions and methods wherein the components are contacted together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

The term "hydrocarbon" whenever used in this specification and claims refers to a compound containing only carbon and hydrogen. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s). The term "alpha olefin" as used herein refers to any olefin that has a double bond between the first and second carbon atom of a contiguous chain of carbon atoms. The term "alpha olefin" includes linear and branched alpha olefins and alpha olefins which have more than one non-aromatic carbon-carbon double bond, unless expressly stated otherwise. The term "normal alpha olefin" as used herein refers to a linear hydrocarbon mono-olefin having a double bond between the first and second carbon atom.

A "polyalphaolefin" (PAO) is a mixture of hydrogenated (or alternatively, substantially saturated) oligomers, containing units derived from an alpha olefin monomer. Unless specified otherwise, the PAO can contain units derived from alpha olefin monomer units, which can be the same (hydrogenated or substantially saturated alpha olefin homo-oligomer) or can be different (hydrogenated or substantially saturated alpha olefin co-oligomer). One having ordinary skill in the art will recognize that depending on the process utilized to produce the PAO, the as-produced alpha olefin oligomers can already be substantially saturated. For example, a process which is carried out in the presence of hydrogen can produce an olefin oligomer which may or may not require a separate hydrogenation step to provide a product with the desired properties.

The term "oligomerization," and its derivatives, refers to processes which produce a mixture of products containing from 2 to 60 olefin monomer units. An "oligomer" is a molecule that contains from 2 to 60 olefin monomer units (per molecule) and an "oligomerization product" or "oligomer product" includes all products made by the "oligomerization" process, including the "oligomers" and products which are not "oligomers" (e.g., products which contain more than 60 monomer units), but excludes non-oligomerized olefin monomer (excludes residual unreacted monomer). It should be noted that the monomer units in the "oligomer" or "oligomerization product" do not have to be the same. For example, these terms are also used generically herein to include olefin homo-oligomers, co-oligomers, and so forth, and thus encompass products derived from any number of different olefin monomers disclosed herein. In like manner, oligomerizing (or oligomerization) is meant to encompasses dimerizing (or dimerization), trimerizing (or trimerization), and so forth.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The oligomerization of monomers comprising a $C_3$ to $C_{30}$ olefin using a chemically-treated solid oxide are disclosed herein. Also disclosed herein are polyalphaolefins (PAO's) having a combination of a high viscosity index and a reduced viscosity at low temperatures (e.g., kinematic viscosity at −40° C.).

Olefin Oligomerizations Processes

Embodiments of this invention are directed to processes for forming an oligomer product. Such oligomerization processes can comprise (or consist essentially of, or consist of) (i) introducing a monomer comprising olefins and a chemically-treated solid oxide into a reaction zone, and (ii) oligomerizing the monomer to form the oligomer product in the reaction zone; or alternatively, (i) introducing a monomer comprising a $C_3$ to $C_{30}$ olefin and a chemically-treated solid oxide into a reaction zone, and (ii) oligomerizing the monomer to form the oligomer product in the reaction zone.

Generally, the features of the processes (e.g., the components and/or features of the monomer, the olefins (e.g., carbon number and/or olefin type, among other olefin features) of the monomer, the chemically-treated solid oxide, and the conditions under which the oligomer product is formed, among others) are independently described herein and these features can be combined in any combination to further describe the disclosed oligomerization processes. Moreover, additional process steps can be performed before, during, and/or after any of the steps of any of the processes disclosed herein, and can be utilized without limitation and in any combination to further describe the oligomerization process, unless stated otherwise.

In some embodiments, the monomer can comprise, consist essentially of, of consist of, $C_3$ to $C_{30}$ olefins. Moreover, the monomer can comprise, consist essentially of, or consist of, any single carbon number olefins from $C_3$ to $C_{30}$ (e.g., $C_6$ olefins) or any combination of different single carbon number olefins from $C_3$ to $C_{30}$ (e.g., $C_3$ to $C_6$ olefins, or $C_8$, $C_{10}$, and $C_{12}$ olefins, among other combinations). Monomers and olefins are described herein and their features can be utilized without limitation to further describe the monomer and olefins which can be utilized in the oligomerization processes. In some embodiments, an oligomerization process can utilize a single chemically-treated solid oxide; or alternatively, the process can utilize more than one chemically-treated solid oxide. Chemically-treated solid oxides are described herein and can be utilized without limitation in the oligomerization processes described herein.

In some embodiments, the introducing step of the process can include adding the monomer, the chemically-treated solid oxide, and additional unrecited materials (e.g., a non-olefin solvent or diluent, a stabilizer, amongst other materials) into a reaction zone. In other embodiments, the introducing step can consist essentially of adding the monomer and the chemically-treated solid oxide into the reaction zone or, alternatively, consist of adding the monomer and the chemically-treated solid oxide into the reaction zone. Likewise, additional materials or features can be employed in the oligomerizing step. For instance, the formation of the oligomer product in the reaction zone can occur in the presence of a non-olefin solvent. The amount of any non-olefin solvent used in addition to the disclosed olefins of the monomer in the introducing step and/or the oligomerizing step of the process is not limited to any particular range. Such solvent, or combination of solvents, can be used, for example, as a flow modifier to alter the flow properties or viscosity of the reaction zone mixture including the monomer (or olefin) and/or the oligomer product. Non-olefin solvents which can be utilized are described herein, and these solvents can be utilized without limitation in the oligomerization processes described herein. In an embodiment, the oligomerization step can be performed in the substantial absence of a solvent (e.g., less than 10, 5, 4, 3, 2, or 1 wt. % solvent, based upon the total weight of the monomer and the solvent).

Independently, the introducing step and the oligomerizing step of the process for forming an oligomer product can be conducted at a variety of temperatures, pressures, and time periods. For instance, the temperature at which the monomer and the chemically-treated solid oxide are introduced into the reaction zone can be the same as, or different from, the temperature at which the oligomer product is formed. As an illustrative example, in the introducing step, the monomer and the chemically-treated solid oxide can be fed into a reaction zone at temperature T1 and, after this initial charging of these materials, the temperature can be changed to a temperature T2 to allow for the oligomerization of the monomer to form the oligomer product. Likewise, the pressure can be different in the introducing step than in the oligomerizing step. Often, the time period in the introducing step can be referred to as the charging time, while the time period in the oligomerizing step can be referred to as the reaction time. The charging time and the reaction time can be, and often are, different.

In an embodiment, the introducing step and/or the oligomerizing step of the process for forming an oligomer product can be conducted at any suitable temperature for the monomer and the chemically-treated solid oxide. For instance, the introducing step and/or the oligomerizing step can be conducted at a minimum temperature of 0° C., 10° C., 15° C., or 20° C.; or alternatively, at a maximum temperature of 250° C., 225° C., 200° C., 180° C., or 150° C. In an embodiment, the introducing step and/or the oligomerizing step can be conducted at a temperature in a range from any minimum temperature disclosed herein to any maximum temperature disclosed herein. In some non-limiting embodiments, the introducing step and/or the oligomerizing step can be conducted at temperature in a range from 0° C. to 250° C.; alternatively, from 0° C. to 200° C.; alternatively, from 10° C. to 250° C.; alternatively, from 10° C. to 225° C.; alternatively, from 15° C. to 225° C.; alternatively, from 15° C. to 200° C.; or alternatively, from 15° C. to 180° C. In other non-limiting embodiments, the contacting step and/or the oligomerizing step can be conducted at a temperature in a range from 10° C. to 200° C., from 20° C. to 200° C., from 20° C. to 180° C., or from 20° C. to 150° C. Other temperature ranges for the introducing step and/or the oligomerizing step are readily apparent from this disclosure. These temperature ranges also are meant to encompass circumstances where either the introducing step, the oligomerizing step, or both, can be conducted at a series of different temperatures, instead of at a single fixed temperature, falling within the respective temperature ranges.

Generally, the oligomerization can be performed at any suitable pressure. While not being limited thereto, the introducing step and/or the oligomerizing step of the process for forming an oligomer product can be conducted at a reactor pressure in a range from 0 to 1000 psig, from 5 to 1000 psig, from 5 to 750 psig, from 5 to 500 psig, from 5 to 250 psig, from 5 to 150 psig, or from 10 to 100 psig. In some embodiments, the introducing step and/or the oligomerizing step can be conducted at atmospheric pressure, while in other embodiments, the introducing step and/or the oligomerizing step can be conducted at sub-atmospheric pressures.

In the oligomerization process, the weight ratio of the monomer to the chemically-treated solid oxide is not particularly limited. In some embodiments, however, the weight ratio can be in a range from 1:1 to 1000:1, from 1:1 to 100:1, or from 2:1 to 1000:1. In other embodiments, the weight ratio can be in a range from 2:1 to 100:1, from 5:1 to 1000:1, or from 5:1 to 100:1. Other weight ratios of the monomer to the chemically-treated solid oxide are readily apparent from this disclosure.

Often, the process for forming the oligomer product can be a flow process and/or a continuous process (e.g., a fixed bed reactor process). In such circumstances, the monomer and chemically-treated solid oxide contact time (or reaction time) can be expressed in terms of weight hourly space velocity (WHSV)—the ratio of the weight of the monomer which comes in contact with a given weight of chemically-treated solid oxide per unit time (units of g/g/hr). While not limited thereto, the WHSV employed for the process of producing an oligomer product can have a minimum value of 0.05, 0.1, 0.25, 0.5, 0.75, or 1; or alternatively, a maximum value of 5, 4, 3, 2.5, or 2. In an embodiment, the WHSV can be in a range from any minimum WHSV disclosed herein to any maximum WHSV disclosed herein.

In a non-limiting example, the WHSV can be in a range from 0.05 to 5; alternatively, from 0.05 to 4; alternatively, from 0.1 to 5; alternatively, from 0.1 to 4; alternatively, from 0.1 to 3; alternatively, from 0.1 to 2; alternatively, from 0.1 to 1; alternatively, from 0.1 to 0.8; alternatively, from 0.5 to 5; alternatively, from 0.5 to 4; alternatively, from 0.5 to 2.5; alternatively, from 0.8 to 3; or alternatively, from 1 to 3. Other WHSV ranges are readily apparent from this disclosure.

The reaction zone can comprise any suitable reactor or vessel in order to form the oligomer product, non-limiting examples of which can include a fixed bed reactor, a stirred tank reactor, a plug flow reactor, and a tubular reactor, including more than one reactor in series or in parallel, and including any combination of reactor types and arrangements. The oligomerization process disclosed herein can be a batch process in some embodiments, while in other embodiments, the oligomerization process can be a continuous process.

In an embodiment, the minimum monomer conversion (or olefin conversion) can be at least 10%, by weight percent or by mole percent. The conversion of the monomer can be described as a "monomer conversion" to indicate that the percentage conversion, in weight percent or in mole percent, is based on the monomer and does not include non-monomer materials that can be present (e.g., solvent, etc.) during the oligomerization. Likewise, for example, the conversion of a monomer (or olefin conversion) comprising a $C_6$ olefin can be described as a "$C_6$ olefin conversion" to indicate that the percentage conversion, in weight percent or in mole percent, is based on the $C_6$ olefin and does not include non-$C_6$ olefin materials that can be present (e.g., solvent, other carbon number olefins, etc.) during the oligomerization. In another embodiment, the minimum monomer conversion (or olefin conversion) can be at least 15%, at least 20%, at least 25%, at least 30%, at least 40%, or at least 50%, and these percentages can be weight percentages or mole percentages. In yet another embodiment, the maximum monomer conversion (or olefin conversion) can be 100%, 95%, 90%, 85%, 80%, 75%, 70%, 65%, 60%, or 55%, and these percentages can be weight percentages or mole percentages. Generally, the monomer conversion (or olefin conversion) can be in a range from any minimum conversion disclosed herein to any maximum conversion disclosed herein. Non-limiting ranges of monomer conversion (or olefin conversion), in weight or mole percentages, can include, but are not limited to, the following ranges: from 10% to 95%, from 10% to 85%, from 10% to 75%, from 10% to 60%, from 15% to 90%, from 15% to 75%, from 20% to 90%, from 20% to 75%, from 30% to 85%, from 30% to 75%, from 40% to 95%, from 40% to 80%, or from 40% to 75%. Other monomer conversion (or olefin conversion) ranges are readily apparent from this disclosure. In some embodiments, these conversions can be achieved in a batch process, while in other embodiments, these conversions can be achieved in a flow or continuous process, such as, for example, multi-passes thru a reactor, such as a fixed bed reactor. Yet, in other embodiments, these conversions can be achieved in a flow or continuous process, such as, for example, a single pass thru a reactor, such as a fixed bed reactor. In such embodiments, the conversions can be described as "single pass conversions" to indicate that the percentage conversions, in weight percent or in mole percent, are based on a single pass thru a reactor or reaction zone.

In an oligomerization process consistent with this invention in which the chemically-treated solid oxide comprises fluorided silica-coated alumina, unexpectedly, a conversion (or single pass conversion) of the monomer to the oligomer product is greater than that of a comparable process using sulfated alumina (i.e., instead of fluorided silica-coated alumina), under the same oligomerization conditions. In particular embodiments, the increase in conversion using fluorided silica-coated alumina instead of sulfated alumina can be at least 10%, at least 20%, at least 30%, at least 40%, at least 50%, at least 75%, or at least 100%, and often up to 150-200%. The percentage increases are based on the conversion using sulfated alumina; for example, if the conversion using sulfated alumina (in weight or mole percentage) was 20% and the conversion using fluorided silica-coated alumina (in the same weight or mole percentage basis as the sulfated alumina) was 30%, then the percentage increase would be a 50% increase.

Similarly, in an oligomerization process consistent with this invention in which the chemically-treated solid oxide comprises fluorided-chlorided silica-coated alumina, unexpectedly, a conversion (or single pass conversion) of the monomer (comprising the $C_3$ to $C_{30}$ olefin, or comprising any single carbon number olefins, or comprising any combination of different single carbon number olefins, etc.) to the oligomer product is greater than that of a comparable process using sulfated alumina (i.e., instead of fluorided-chlorided silica-coated alumina), under the same oligomerization conditions. In particular embodiments, the increase in conversion using fluorided-chlorided silica-coated alumina instead of sulfated alumina can be at least 10%, at least 20%, at least 30%, at least 40%, at least 50%, at least 75%, or at least 100%, and often up to 150-200%. The percentage increases are based on the conversion using sulfated alumina; for example, if the conversion using sulfated alumina (in weight or mole percentage) was 20% and the conversion using fluorided-chlorided silica-coated alumina (in the same weight or mole percentage basis as the sulfated alumina) was 25%, then the percentage increase would be a 25% increase.

Monomers Containing Olefins

Embodiments of this invention are directed to processes comprising introducing a monomer comprising a $C_3$ to $C_{30}$ olefin and a chemically-treated solid oxide into a reaction zone, and oligomerizing the monomer to form an oligomer product in the reaction zone. A wide range of monomers comprising, consisting essentially of, or consisting of, $C_3$ to $C_{30}$ olefins can be oligomerized according to the methods provided herein, and using the chemically-treated solid oxides disclosed herein. In any embodiment, the monomer can comprise internal olefins and/or the monomer can comprise alpha olefins. Further, the alpha olefins can comprise, or consist essentially of, normal alpha olefins. Consequently, in some embodiments, the oligomerization processes disclosed herein can employ a monomer which is a mixture of internal olefins and alpha olefins. In particular embodiments, the monomer can comprise, or consist essentially of, normal alpha olefins.

Generally, the monomer can comprise (or consist essentially of, or consist of) $C_3$ to $C_{30}$ olefins, or alternatively, $C_3$ to $C_{18}$ olefins. In one embodiment, the monomer can comprise (or consist essentially of, or consist of) $C_3$ to $C_5$ olefins, while in another embodiment, the monomer can comprise (or consist essentially of, or consist of) $C_6$ to $C_{18}$ olefins, or $C_8$ to $C_{12}$ olefins. In yet another embodiment, the monomer can comprise $C_3$ to $C_8$ olefins, $C_{10}$ to $C_{18}$ olefins, $C_6$ to $C_{16}$ olefins, or $C_{12}$ to $C_{16}$ olefins. In other embodiments, the monomer can comprise (or consist essentially of, or consist of) $C_3$ olefins; alternatively, $C_6$ olefins; alternatively, $C_8$ olefins; alternatively, $C_{10}$ olefins; alternatively, $C_{12}$ olefins;

alternatively, $C_{14}$ olefins; alternatively, $C_{16}$ olefins; or alternatively, $C_{18}$ olefins. Thus, mixtures of olefins having different numbers of carbon atoms can be used, or olefins having predominantly a single number of carbon atoms can be used as the monomer.

In an embodiment, the monomer can comprise at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, at least 92.5 wt. %, or at least 95 wt. % of any olefin, olefin carbon number range, or mixture of olefins described herein. Additionally or alternatively, the monomer can comprise a maximum of 100 wt. %, 99 wt. %, 98 wt. %, 97 wt. %, or 96 wt. %, of any olefin, olefin carbon number range, or mixture of olefins described herein. Generally, the weight percent can be in a range from any minimum weight percent disclosed herein to any maximum weight percent disclosed herein. Therefore, non-limiting monomer weight percent ranges can include, but are not limited to, the following ranges: from 50 to 100 wt. %, from 55 to 99 wt. %, from 60 to 98 wt. %, from 65 to 97 wt. %, from 70 to 96 wt. %, from 75 to 100 wt. %, from 80 to 100 wt. %, or from 80 to 98 wt. % of any olefin, olefin carbon number range, or mixture of olefins described herein. Other monomer weight percent ranges are readily apparent from this disclosure.

In these and other embodiments, the olefins can be cyclic or acyclic, and/or linear or branched. For example, the monomer can comprise, consist essentially of, or consist of, cyclic olefins; additionally or alternatively, the monomer can comprise, consist essentially of, or consist of, linear olefins. Moreover, the monomer can comprise olefins having only one olefin moiety (mono-olefins) and/or olefins having two olefin moieties (di-olefins), as well as compounds having more than two olefin moieties per molecule; alternatively, mono-olefins; alternatively, di-olefins; or alternatively, olefins having more than two olefin moieties per molecule.

The monomer can comprise linear and/or branched olefins, and therefore, mixtures of linear and branched olefins can be used. Suitable branched olefins can, for example, have a branch at any position and can have the double bond at any suitable position. In one embodiment, the branched olefin can have more than one branch. In another embodiment, the branched olefin can have one or more branches at the carbon-carbon double bond; or alternatively, the branched olefin can have one or more branches on carbon atoms that are not part of a carbon-carbon double bond. In yet another embodiment, the olefins can comprise, consist essentially of, or consist of, linear olefins.

In further embodiments, the monomer can comprise (or consist essentially of, or consist of) $C_3$ to $C_{30}$ alpha olefins (or normal alpha olefins), or alternatively, $C_3$ to $C_{18}$ alpha olefins (or normal alpha olefins). In one embodiment, for example, the monomer can comprise (or consist essentially of, or consist of) $C_3$ to $C_5$ alpha olefins (or normal alpha olefins), while in another embodiment, the monomer can comprise (or consist essentially of, or consist of) $C_6$ to $C_{18}$ alpha olefins (or normal alpha olefins), or $C_8$ to $C_{12}$ alpha olefins (or normal alpha olefins). In yet another embodiment, the monomer can comprise $C_3$ to $C_8$ alpha olefins (or normal alpha olefins), $C_{10}$ to $C_{18}$ alpha olefins (or normal alpha olefins), $C_6$ to $C_{16}$ alpha olefins (or normal alpha olefins), or $C_{12}$ to $C_{16}$ alpha olefins (or normal alpha olefins). In other embodiments, the monomer can comprise (or consist essentially of, or consist of) propylene, 1-butene, 1-pentene, or any combination thereof; alternatively, propylene; alternatively, 1-butene; or alternatively, 1-pentene. Yet, in other embodiments, the monomer can comprise (or consist essentially of, or consist of) 1-hexene, 1-octene, 1-decene, 1-dodecene, 1-tetradecene, 1-hexadecene, or any combination thereof; alternatively, 1-octene, 1-decene, 1-dodecene, or any combination thereof; alternatively, 1-hexene; alternatively, 1-octene; alternatively, 1-decene, alternatively, 1-dodecene; alternatively, 1-tetradecene; or alternatively, 1-hexadecene. Thus, mixtures of alpha olefins (or normal alpha olefins) having different numbers of carbon atoms can be used, or alpha olefins (or normal alpha olefins) having predominantly a single number of carbon atoms can be used as the monomer.

Moreover, as above, the monomer can contain any suitable amount of any olefin, olefin carbon number range, or mixture of olefins described herein. For instance, the monomer can contain from 50 to 100 wt. %, from 55 to 99 wt. %, from 60 to 98 wt. %, from 65 to 97 wt. %, from 70 to 96 wt. %, from 75 to 100 wt. %, from 80 to 100 wt. %, or from 80 to 98 wt. % $C_3$ to $C_{30}$ alpha olefins (or normal alpha olefins); alternatively, alpha olefins (or normal alpha olefins) of any carbon number range described herein; alternatively, of any combination of single carbon numbered alpha olefins (and/or normal alpha olefins) described herein; or alternatively, of any single carbon numbered alpha olefins (or normal alpha olefins) described herein. Additionally, other monomer weight percent ranges are readily apparent from this disclosure. For instance, in a non-limiting example, the monomer can comprise can comprise at least 75 wt. %, at least 80 wt. %, at least 85 wt. %, at least 90 wt. %, or at least 95 wt. %, of propylene; alternatively, 1-hexene; alternatively, 1-octene; alternatively, 1-decene; alternatively, 1-dodecene; alternatively, 1-tetradecene; or alternatively, 1-hexadecene.

As described herein, the monomer can comprise various carbon number ranges and/or types of olefins. The various carbon numbers of the olefin(s), the type of olefin(s), and the weight percentage of the olefin(s) can be combined in any fashion to describe the monomer or olefin(s) that can be used in the oligomerization processes of this invention.

Chemically-Treated Solid Oxides

In the processes disclosed herein, a monomer and a chemically-treated solid oxide can be introduced into a reaction zone, and the monomer can be oligomerized to form an oligomer product in the reaction zone. Any suitable chemically-treated solid oxide can be employed in this invention, whether one chemically-treated solid oxide or a mixture or combination of two or more different chemically-treated solid oxides. In accordance with particular embodiments of this invention, the oligomerizing step can be conducted in the substantial absence of organoaluminum compounds, metallocene compounds, or both organoaluminum and metallocene compounds (e.g., less than 5, 4, 3, 2, 1, or 0.5 wt. % organoaluminum compounds, metallocene compounds, or both organoaluminum and metallocene compounds, based upon the weight of the chemically-treated solid oxide).

In one embodiment, the chemically-treated solid oxide can comprise a solid oxide treated with an electron-withdrawing anion. Alternatively, in another embodiment, the chemically-treated solid oxide can comprise a solid oxide treated with an electron-withdrawing anion, the solid oxide containing a Lewis-acidic metal ion. Non-limiting examples of suitable chemically-treated solid oxides are disclosed in, for instance, U.S. Pat. Nos. 7,294,599, 7,601,665, 7,884, 163, 8,309,485, 8,623,973, 8,703,886, and 9,023,959.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form a chemically-treated solid oxide, either singly or in combination, can include, but are not limited to, silica-alumina, silica-titania, silica-zirconia, alumina-titania, alumina-zirconia, zinc-aluminate, alumina-boria, silica-boria, aluminophosphate-silica, and titania-zirconia. The solid oxide used herein also can encompass oxide materials such as silica-coated alumina, as described in U.S. Pat. No. 7,884,163.

Accordingly, in one embodiment, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another embodiment, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another embodiment, the solid oxide can comprise silica, alumina, titania, zirconia, magnesia, boria, zinc oxide, any mixed oxide thereof, or any combination thereof. In yet another embodiment, the solid oxide can comprise silica-alumina, silica-coated alumina, silica-titania, silica-zirconia, alumina-boria, or any combination thereof. In still another embodiment, the solid oxide can comprise silica, alumina, silica-alumina, silica-coated alumina, or any mixture thereof; alternatively, silica; alternatively, alumina; alternatively, silica-alumina; or alternatively, silica-coated alumina.

The silica-alumina or silica-coated alumina solid oxide materials which can be used can have a silica content from 5 to 95% by weight. In one embodiment, the silica content of these solid oxides can be from 10 to 80%, or from 20% to 70%, silica by weight. In another embodiment, such materials can have silica contents ranging from 15% to 60%, from 25% to 50%, from 25% to 48%, or from 20% to 45%, silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one embodiment, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, and molybdate, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, or any combination thereof, in some embodiments provided herein. In other embodiments, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof. Yet, in other embodiments, the electron-withdrawing anion can comprise sulfate, fluoride, chloride, or combinations thereof; alternatively, sulfate; alternatively, fluoride and chloride; or alternatively, fluoride.

The chemically-treated solid oxide generally can contain from 1 to 25 wt. % of the electron-withdrawing anion, based on the weight of the chemically-treated solid oxide. In particular embodiments provided herein, the chemically-treated solid oxide can contain from 1 to 20 wt. %, from 2 to 20 wt. %, from 3 to 20 wt. %, from 2 to 15 wt. %, from 3 to 15 wt. %, from 3 to 12 wt. %, or from 4 to 10 wt. %, of the electron-withdrawing anion, based on the total weight of the chemically-treated solid oxide.

In an embodiment, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, as well as any mixture or combination thereof. In another embodiment, the chemically-treated solid oxide employed herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, as well as combinations thereof. In yet another embodiment, the chemically-treated solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some embodiments, the chemically-treated solid oxide can comprise a fluorided solid oxide, while in other embodiments, the chemically-treated solid oxide can comprise a sulfated solid oxide.

Various processes can be used to form chemically-treated solid oxides useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485. Other suitable processes and procedures for preparing chemically-treated solid oxides (e.g., fluorided solid oxides, sulfated solid oxides, etc.) are well known to those of skill in the art.

Non-Olefin Solvents

Illustrative non-olefin organic solvents which can be utilized in the processes disclosed herein can include aliphatic hydrocarbons, petroleum distillates, or combinations thereof; alternatively, aliphatic hydrocarbons; or alternatively, petroleum distillates. Generally, suitable solvents include solvents that do not react with the monomers, olefins, alpha olefins, etc., disclosed herein. In an embodiment, any solvent described herein can be substantially devoid of water (e.g., less than 100, 75, 50, 25, 10, 5, or 1 ppm water by weight).

Aliphatic hydrocarbons which can be useful as an oligomerization solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified.

Non-limiting examples of suitable acyclic aliphatic hydrocarbon solvents that can be utilized singly or in any combination include pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; hexane (n-hexane or a mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons).

Non-limiting examples of suitable cyclic aliphatic hydrocarbon solvents include cyclohexane, methyl cyclohexane, and combinations thereof; alternatively cyclohexane; or alternatively, methylcyclohexane.

Oligomer Products and Polyalphaolefins

Embodiments of the present invention also are directed to oligomer products produced from a monomer comprising an olefin. For instance, the present invention encompasses any oligomer product produced by a process comprising (i) introducing a monomer comprising an olefin and a chemically-treated solid oxide into a reaction zone, and (ii) oligomerizing the monomer to form the oligomer product in the reaction zone. Features and characteristics of the monomer comprising the olefin and of the chemically-treated solid oxide are described herein.

It is contemplated that the oligomerization processes disclosed herein have excellent olefin conversions and selectivity to desired oligomer product fractions, such as dimers and/or trimers. In one embodiment, for example, the monomer can comprise propylene, and the oligomer product can be characterized by a total trimer/tetramer content of at least 70 wt. %, at least 75 wt. %, at least 80 wt. %, from 70 to 95 wt. %, or from 70 to 90 wt. %. Additionally or alternatively, this oligomer product can be characterized by at least 30 wt. %, at least 40 wt. %, at least 45 wt. %, from 35 to 60 wt. %, or from 40 to 55 wt. % trimers. Additionally or alternatively, this oligomer product can be characterized by a weight ratio of trimers to tetramers in the oligomer product of greater than 1:1, e.g., a trimer:tetramer weight ratio in a range from 1.05:1 to 1.6:1, or from 1.1:1 to 1.5:1.

In another embodiment, the monomer can comprise 1-butene, 1-pentene, 1-hexene, or any combination thereof, and the oligomer product can be characterized by a total dimer/trimer content of at least 70 wt. %, at least 80 wt. %, at least 85 wt. %, from 70 to 98 wt. %, or from 75 to 97 wt. %. Additionally or alternatively, this oligomer product can be characterized by at least 30 wt. %, at least 40 wt. %, at least 45 wt. %, from 35 to 65 wt. %, or from 40 to 65 wt. % trimers. Additionally or alternatively, this oligomer product can be characterized by a weight ratio of trimers to dimers in the oligomer product of in a range from 0.5:1 to 2:1, or a weight ratio greater than 1:1, e.g., a trimer:dimer weight ratio in a range from 1.02:1 to 2:1, or from 1.05:1 to 2:1.

In another embodiment, the monomer can comprise a $C_8$ to $C_{12}$ olefin (e.g., 1-octene, 1-decene, 1-dodecene, or any combination thereof), and the oligomer product can be characterized by a dimer content of at least 30 wt. %, at least 55 wt. %, at least 60 wt. %, from 30 to 98 wt. %, from 55 to 95 wt. %, or from 60 to 88 wt. %. Additionally or alternatively, this oligomer product can be characterized by a weight ratio of dimers to trimers in the oligomer product of greater than 1:1, greater than 1.5:1, or greater than 2:1, e.g., a dimer:trimer weight ratio in a range from 1.5:1 to 8:1, from 1.5:1 to 6:1, from 1.5:1 to 4:1, from 2:1 to 8:1, from 2:1 to 6:1, or from 2:1 to 4:1.

In an embodiment of this invention, the oligomer product (alternatively, dimers; alternatively, trimers; alternatively, tetramers; or alternatively, any fraction comprising all or any portion of the oligomer product) can be isolated, e.g., from the reactor effluent of the oligomerization process. For instance, any process disclosed herein can further comprise a step of removing a reactor effluent from the reaction zone, and separating at least a portion of the chemically-treated solid oxide from the reactor effluent. Additionally or alternatively, any process disclosed herein can further comprise a step of removing at least a portion of the monomer from the reactor effluent. As would be recognized by one of skill in the art, these steps can be performed using any suitable technique, such as filtration, evaporation, or distillation, as well as combinations of two or more of these techniques.

The processes disclosed herein can further comprise a step of isolating one or more fractions comprising all or a portion of the oligomer product. For instance and not limited thereto, a dimer fraction can be isolated, a trimer fraction can be isolated, a dimer and trimer fraction can be isolated, a trimer and tetramer fraction can be isolated, a trimer and heavier oligomer fraction can be isolated, and so forth. This isolation step can be performed using any suitable technique, such as filtration, evaporation, or distillation, as well as combinations of two or more of these techniques, and these techniques can be performed at atmospheric or any suitable sub-atmospheric pressure.

Further, the oligomer product (alternatively, dimers; alternatively, trimers; alternatively, tetramers; or alternatively, any fraction comprising all or any portion of the oligomer product) can be hydrogenated. Thus, any of the processes described herein optionally can further comprise a step of hydrogenating the oligomer product (alternatively, dimers; alternatively, trimers; alternatively, tetramers; or alternatively, any fraction comprising all or any portion of the oligomer product). Suitable hydrogenation procedures and associated metal catalysts (e.g., platinum, rhenium, palladium, nickel, etc.) are well known to those of skill in the art. Alternatively, the oligomer product (or a large fraction thereof) can be hydrogenated first, and then isolated into one or more fractions, e.g., a hydrogenated dimer fraction, a hydrogenated trimer fraction, a hydrogenated dimer and trimer fraction, a hydrogenated trimer and tetramer fraction, a hydrogenated trimer and heavier oligomer fraction, and the like. The hydrogenated oligomer product, any hydrogenated oligomer product fraction, or any fraction of the hydrogenated oligomer product, can be referred to as a polyalphaolefin.

Embodiments of the present invention also are directed to and encompass any oligomer product (alternatively, dimers; alternatively, trimers; alternatively, tetramers; or alternatively, any fraction comprising all or any portion of the oligomer product) or any polyalphaolefin produced by any of the processes disclosed herein. The oligomer product and the polyalphaolefin can have any suitable kinematic viscosity at 100° C., for instance, ranging from 1.8 to 12 cSt, from 1.8 to 10.4 cSt, from 1.8 to 8.4 cSt, from 1.8 to 6.4 cSt, or from 1.8 to 4.4 cSt. Accordingly, fractions comprising all or any portion of the oligomer product and all or any portion of the polyalphaolefin can have a kinematic viscosity at 100° C. that generally can fall within a range from 1.8 cSt to 2.2 cSt, from 2.3 cSt to 2.7 cSt, from 2.6 cSt to 3.4 cSt, from 3.6 cSt to 4.4 cSt, from 4.6 cSt to 5.4 cSt, from 5.6 cSt to 6.4 cSt, from 6.6 cSt to 7.4 cSt, from 7.6 cSt to 8.4 cSt, from 8.6 cSt to 9.4 cSt, or from 9.6 cSt to 10.4 cSt, as well as combination thereof.

This invention also contemplates and encompasses any compositions (e.g., lubricant compositions or lubricant formulations) or base oils that comprise the oligomer products (alternatively, dimers; alternatively, trimers; alternatively, tetramers; or alternatively, any fraction comprising all or any portion of the oligomer products) or polyalphaolefins produced or described herein.

An illustrative and non-limiting example of a polyalphaolefin of the present invention can comprise at least 80 wt. % hydrogenated oligomers of a $C_6$ to $C_{12}$ alpha olefin (or any other alpha olefin, any alpha olefin range, or mixture of alpha olefins described herein, such as one or more $C_6$ to $C_{12}$ alpha olefins, or one or more $C_6$ to $C_{12}$ normal alpha olefins), and the polyalphaolefin can be characterized by a viscosity index greater than or equal to 110 and a kinematic viscosity at −40° C. of less than or equal to 1750 cSt. The polyalphaolefin can further comprise hydrogenated dimers and trimers at any suitable weight ratio of hydrogenated dimers:trimers, for instance, greater than 2:1; alternatively, greater than 2.5:1; alternatively, greater than 3:1; alternatively, from 2:1 to 6:1; or alternatively, from 2.5:1 to 5:1.

Another illustrative and non-limiting example of a polyalphaolefin of the present invention can comprise at least 30 wt. % $C_{24}$ saturated hydrocarbons (or at least 50 wt. %, or at least 75 wt. %, or at least 85 wt. %), and the polyalphaolefin can be characterized by a viscosity index greater than or equal to 110 and a kinematic viscosity at −40° C. of less than or equal to 1750 cSt. The polyalphaolefin can further comprise $C_{36}$ saturated hydrocarbons, and a weight ratio of $C_{24}$:$C_{36}$ saturated hydrocarbons can be in any suitable range, such as greater than 2:1; alternatively, greater than 2.5:1; alternatively, greater than 3:1; alternatively, from 2:1 to 6:1; or alternatively, from 2.5:1 to 5:1. Moreover, another illustrative and non-limiting example of a polyalphaolefin of the present invention can comprise at least 30 wt. % $C_{20}$ saturated hydrocarbons (or at least 50 wt. %, or at least 75 wt. %, or at least 85 wt. %), and the polyalphaolefin can be characterized by a viscosity index greater than or equal to 110 and a kinematic viscosity at −40° C. of less than or equal to 1750 cSt. The polyalphaolefin can further comprise $C_{30}$ saturated hydrocarbons, and a weight ratio of $C_{20}$:$C_{30}$ saturated hydrocarbons can be in any suitable range, such as greater than 2:1; alternatively, greater than 2.5:1; alternatively, greater than 3:1; alternatively, from 2:1 to 6:1; or alternatively, from 2.5:1 to 5:1.

These illustrative and non-limiting examples of polyalphaolefins consistent with the present invention also can have any of the characteristics or properties provided below, and in any combination.

In an embodiment, the polyalphaolefin can have a viscosity index in a range from 110 to 150. Other suitable non-limiting ranges for the viscosity index can include the following ranges: from 110 to 125, from 110 to 120, from 112 to 150, from 112 to 125, or from 112 to 120. Other appropriate ranges for the viscosity index of the polyalphaolefin are readily apparent from this disclosure. The viscosity index is measured in accordance with ASTM D7042-04.

In an embodiment, the polyalphaolefin can have a kinematic viscosity at −40° C. in a range from 1200 to 1750 cSt. Other suitable non-limiting ranges for the kinematic viscosity at −40° C. can include the following ranges: from 1300 to 1750 cSt, from 1400 to 1750 cSt, from 1300 to 1700 cSt, from 1400 to 1700 cSt, from 1350 to 1700 cSt, from 1350 to 1650 cSt, or from 1350 to 1550 cSt. Other appropriate ranges for the kinematic viscosity at −40° C. of the polyalphaolefin are readily apparent from this disclosure. Kinematic viscosities are measured in accordance with ASTM D7042-04 (Stabinger Method).

In an embodiment, the polyalphaolefin can have a kinematic viscosity at 40° C. in a range from 9 to 18 cSt. Other suitable non-limiting ranges for the kinematic viscosity at 40° C. can include the following ranges: from 9 to 15 cSt, from 9 to 14 cSt, from 10 to 18 cSt, from 10 to 15 cSt, from 11 to 18 cSt, from 11 to 15 cSt, or from 11 to 14 cSt. Other appropriate ranges for the kinematic viscosity at 40° C. of the polyalphaolefin are readily apparent from this disclosure.

In an embodiment, the polyalphaolefin can have a kinematic viscosity at 100° C. in a range from 1.8 to 12 cSt. Other suitable non-limiting ranges for the kinematic viscosity at 100° C. can include the following ranges: from 1.8 to 10.4 cSt, from 1.8 to 8.4 cSt, from 1.8 to 6.4 cSt, from 1.8 to 4.4 cSt, from 2.5 to 6.4 cSt, from 2.5 to 4.4 cSt, or from 3 to 4.4 cSt. Other appropriate ranges for the kinematic viscosity at 100° C. of the polyalphaolefin are readily apparent from this disclosure.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Chemically-Treated Solid Oxide Preparation

The chemically-treated solid oxides were prepared as follows. For sulfated alumina, Alumina A from W.R. Grace, having a surface area of about 300 m²/g and a pore volume of about 1.2 mL/g, was used. After calcining in a muffle furnace for 12 hours at 600° C., the alumina was allowed to cool. Then, the calcined alumina was impregnated with a solution of sulfuric acid in methanol, such that 3 mL of methanol were added per gram of alumina. The methanol contained enough sulfuric acid to equal about 15% sulfate based on the weight of the sulfated alumina. This sulfate-impregnated alumina was then placed in a flat pan and allowed to dry under vacuum at approximately 110° C. for about 16 hours. To calcine the support, about 10 g of the powdered mixture were placed in a 1.75-inch quartz tube fitted with a sintered quartz disk at the bottom. While the powder was supported on the disk, dry air (dried by passing through a 13× molecular sieve column) was blown upward through the disk at a rate of about 1.6 to 1.8 standard cubic feet per hour; dry nitrogen can be substituted for dry air. An electric furnace around the quartz tube was then turned on and the temperature was raised at the rate of about 400° C. per hour to the desired calcining temperature of about 600° C. (except Examples 6-9, which used different calcining temperatures). At this calcining temperature, the powder was allowed to fluidize for about three hours in the dry air. Afterward, the sulfated alumina was collected and stored under dry nitrogen, and was used without exposure to the atmosphere.

Silica-coated aluminas were prepared as follows. The same alumina (Alumina A) used in preparing sulfated alumina was first calcined at about 600° C. for approximately 6 hours, cooled to ambient temperature, and then contacted with tetraethylorthosilicate in isopropanol to equal 25 wt. % $SiO_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina was collected and stored under dry nitrogen, and was used without exposure to the atmosphere.

Fluorided-chlorided silica-coated aluminas (4 wt. % Cl+7 wt. % F) were produced by first calcining the silica-coated alumina at 600° C. for 3 hours. The chloriding step involved injecting and vaporizing $CCl_4$ into an air stream (typically, over a time period of less than about 5 minutes) used to fluidize the silica-coated alumina during calcination at a peak chloriding temperature of 500° C. (total duration of the calcining operation was 4 hours). The fluoriding step involved injecting and vaporizing tetrafluoroethane into the air stream (typically, over a time period of less than about 5 minutes) used to fluidize the chlorided silica-coated alumina during calcination at a peak fluoriding temperature of 500° C. (total duration of the calcining operation was 4.5 hours).

Olefin Oligomerizations

Gas chromatographic (GC) analyses were performed using a split injection method on an HP 5890 gas chromatograph with a flame ionization detector (FID). Initial oven temperature was 100° C. for 2 minutes and increased 8° C./min to 185° C., then 20° C./min to 290° C. for 6 minutes. The column was an HP-1 column, 12 m×0.2 mm×0.33 μm. Data analysis was performed using Chemstation® software.

Examples 1-5

Oligomerization of 1-dodecene with Sulfated Alumina at Different Reaction Temperatures and Times Examples 1-4 were conducted as follows. In an inert atmosphere drybox, a previously dried 50 mL 3-necked round-bottom flask was charged with 0.503 grams of sulfated alumina and a magnetic stir bar. The necks of the round-bottom flask were then fitted with rubber septa and transferred from the drybox to a fume hood. The round-bottom flask was then placed on a heating mantle on the top of a magnetic stirrer. One of the rubber septa was then equipped with a needle connected to a positive source of nitrogen inflow and a thermocouple. A second rubber septa was equipped with a needle connected to a bubbler so as to maintain a nitrogen atmosphere within the round-bottom flask.

For Examples 1A-1C, the reaction was initiated by charging 20 mL (15.94 g) of 1-dodecene, by syringe, into the round-bottom flask containing 0.5 g of sulfated alumina. Stirring of the reaction was initiated and the reaction mixture was heated to 110° C. Liquid samples were then removed from the round-bottom flask, by syringe, at (1A) 38 minutes, (1B) 2 hours, and (1C) 4.5 hours of reaction time. The contents of the round-bottom flask were then allowed to cool to room temperature and the stirring of the reaction mixture was terminated. The liquid samples were then analyzed by gas chromatography to determine composition of the reaction mixture. Table I provides the compositional make-up of the liquid samples.

For Examples 2A-2C, the reaction was initiated by charging 20 mL (15.94 g) of 1-dodecene, by syringe, into the round-bottom flask containing 0.5 g of sulfated alumina. Stirring of the reaction was initiated and the reaction mixture was heated to 150° C. Liquid samples were then removed from the round-bottom flask, by syringe, at (2A) 34 minutes, (2B) 2 hours and 43 minutes, and (2C) 4.5 hours of reaction time. The contents of the round-bottom flask were then allowed to cool to room temperature and the stirring of the reaction mixture was terminated. The liquid samples were then analyzed by gas chromatography to determine composition of the reaction mixture. Table I provides the compositional make-up of the liquid samples.

For Examples 3A-3D, the reaction was initiated by charging 20 mL (15.94 g) of 1-dodecene, by syringe, into the round-bottom flask containing 0.5 g of sulfated alumina. Stirring of the reaction was initiated and the reaction mixture was heated to 200° C. Liquid samples were then removed from the round-bottom flask, by syringe, at (3A) 30 minutes (188° C.), (3B) 58 minutes (201° C.), (3C) 2 hours (201° C.), and (3D) 4 hours and 12 minutes (206° C.) of reaction time. The contents of the round-bottom flask were then allowed to cool to room temperature and the stirring of the reaction mixture was terminated. The liquid samples were then analyzed by gas chromatography to determine composition of the reaction mixture. Table I provides the compositional make-up of the liquid samples.

For Examples 4A-4C, the reaction was initiated by charging 20 mL (15.94 g) of 1-dodecene, by syringe, into the round-bottom flask containing 0.5 g of sulfated alumina. Stirring of the reaction was initiated and the reaction mixture was heated to 150° C. Liquid samples were then removed from the round-bottom flask, by syringe, at (4A) 49 minutes, (4B) 2 hours, and (4C) 4 hours of reaction time. The contents of the round-bottom flask were then allowed to cool to room temperature and the stirring of the reaction mixture was terminated. The liquid samples were then analyzed by gas chromatography to determine composition of the reaction mixture. Table I provides the compositional make-up of the liquid samples.

Example 5 was conducted as follows. A dry 3-necked round-bottom flask equipped with a mechanical stirrer, a thermocouple, a nitrogen inlet, and a nitrogen outlet connected to a bubbler, was charged, under nitrogen atmosphere, with 500 mL of previously dried 1-dodecene. The contents of round-bottom flask were then heated, with stirring, to 100° C. A sample of 14.315 grams of sulfated alumina, which had been dried in a vacuum oven over night at 240° C., was quickly removed from the vacuum oven and charged to the round-bottom flask under a nitrogen atmosphere. The reaction mixture was then heated to 150° C. and stirred. Liquid samples were then removed from the round-bottom flask, by syringe, at (5A) 58 minutes, (5B) 1 hour and 54 minutes, (5C) 3 hours and 3 minutes, and (5D) 4 hours and 13 minutes of reaction time. The contents of the round-bottom flask were then allowed to cool to room temperature and the stirring of the reaction mixture was terminated. The liquid samples were then analyzed by gas chromatography to determine composition of the reaction mixture. Table I provides the compositional make-up of the liquid samples. The oligomer product of Example 5 had a 100° C., 40° C., and −40° C. kinematic viscosities of 3.2 cSt, 12.7 cSt, and 1,445 cSt, respectively. The viscosity index of the oligomer product was 114. The kinematic viscosity and viscosity index for the oligomer product of Example 5 were determined using ASTM D7042-04.

In Table I, Examples 1-5 are summarized. The product compositions are shown in wt. %, dimer/trimer is the dimer:trimer ratio in the oligomer product, dimer yield is the percentage of the dimer in the oligomer product, and the calculated viscosity at 100° C. is provided in cSt. The calculated viscosity was determined using a proprietary program that correlates oligomer distribution with kinematic viscosity to provide a calculated kinematic viscosity based on known oligomer distributions.

As shown in Table I, regardless of the reaction temperature, monomer conversion increased with reaction time for all of the examples, and the amount of dimer also increased with reaction time for all of the examples. Dimer yield was unexpectedly high for all examples, with about 63-81 wt. % of the oligomer product (excluding residual monomer) being the $C_{24}$ dimer. Moreover, the sulfated alumina catalyst had surprisingly high selectivity to the dimer, with ratios of dimer:trimer generally ranging from 2.6:1 to 5.3:1.

Examples 6-9

Oligomerization of 1-dodecene with Sulfated Alumina Calcined at Different Temperatures Examples 6-9 were conducted using the method as described above for Examples 1-4 at a reaction temperature of 150° C., and the liquid samples were then analyzed by gas chromatography to determine composition of the reaction mixture. Table II provides the compositional make-up of the liquid samples. The sulfated alumina was either (Example 6) not calcined, (Example 7) calcined at 100° C., (Example 8) calcined at 200° C., or (Example 9) calcined at 300° C. For Example 6, liquid samples were removed, by syringe, at (6A) 15 minutes, (6B) 30 minutes, (6C) 1 hour, and (6D) 2 hours of reaction time. For Example 7, liquid samples were removed, by syringe, at (7A) 15 minutes, (7B) 30 minutes, (7C) 1 hour, and (7D) 2 hours of reaction time. For Example 8, liquid samples were removed, by syringe, at (8A) 15 minutes, (8B) 30 minutes, (8C) 1 hour, and (8D) 2 hours of reaction time. For Example 9, liquid samples were removed, by syringe, at (9A) 15 minutes, (9B) 30 minutes, (9C) 1 hour, and (9D) 2 hours of reaction time.

In Table II, Examples 6-9 are summarized. The product compositions are shown in wt. %, dimer/trimer is the dimer:trimer ratio in the oligomer product, dimer yield is the percentage of the dimer in the oligomer product (excluding residual monomer), and the calculated viscosity at 100° C. is provided in cSt. Regardless of the calcination temperature, monomer conversion increased with reaction time for all of the examples, and the amount of dimer also increased with reaction time for all of the examples. Dimer yield was unexpectedly high for all examples, with about 66-85 wt. % of the oligomer product (excluding residual monomer) being the $C_{24}$ dimer. Moreover, the sulfated alumina catalyst had surprisingly high selectivity to the dimer regardless of calcination temperature, with ratios of dimer:trimer generally ranging from 2.6:1 to 6.9:1.

TABLE I

Summary of Examples 1-5.

| Example | Time | Temp (° C.) | Composition | | | | | | | Dimer/Trimer | Dimer Yield | Calc. Viscosity |
| --- | --- | --- | --- | --- | --- | --- | --- | --- | --- | --- | --- | --- |
| | | | $C_{12}$ | $C_{24}$ | $C_{36}$ | $C_{48}$ | $C_{60}$ | $C_{72}$ | $C_{84}$ | | | |
| 1A | 0:38 | 110 | 55.9% | 30.3% | 9.4% | 2.68% | 0.98% | 0.71% | 0.00% | 3.2 | 69% | 3.18 |
| 1B | 2:00 | 110 | 40.6% | 39.4% | 13.2% | 4.26% | 1.47% | 0.55% | 0.47% | 3.0 | 66% | 3.27 |
| 1C | 4:30 | 110 | 28.5% | 45.3% | 17.4% | 5.92% | 1.86% | 0.65% | 0.38% | 2.6 | 63% | 3.35 |
| 2A | 0:30 | 150 | 54.5% | 34.4% | 7.8% | 2.24% | 0.67% | 0.33% | | 4.4 | 76% | 2.97 |
| 2B | 2:43 | 150 | 33.7% | 46.7% | 14.0% | 3.91% | 1.06% | 0.43% | 0.24% | 3.3 | 70% | 3.11 |
| 2C | 4:30 | 150 | 25.8% | 50.1% | 17.5% | 4.82% | 1.22% | 0.38% | 0.12% | 2.9 | 68% | 3.17 |
| 3A | 0:30 | 188 | 72.5% | 19.0% | 5.9% | 1.72% | 0.47% | 0.17% | | 3.2 | 69% | 3.12 |
| 3B | 0:58 | 201 | 57.9% | 32.3% | 7.4% | 1.82% | 0.48% | 0.15% | | 4.4 | 77% | 2.92 |
| 3C | 2:00 | 201 | 41.8% | 43.2% | 11.4% | 2.72% | 0.65% | 0.33% | | 3.8 | 74% | 2.98 |
| 3D | 4:12 | 206 | 28.0% | 49.0% | 17.4% | 4.28% | 1.04% | 0.23% | 0.05% | 2.8 | 68% | 3.14 |
| 4A | 0:49 | 150 | 77.4% | 15.7% | 5.0% | 1.47% | 0.39% | 0.09% | | 3.1 | 69% | 3.12 |
| 4B | 2:00 | 150 | 74.6% | 19.1% | 4.6% | 1.29% | 0.35% | 0.09% | | 4.1 | 75% | 2.92 |
| 4C | 4:00 | 150 | 66.7% | 26.0% | 5.5% | 1.43% | 0.34% | 0.06% | | 4.8 | 78% | 3.14 |
| 5A | 0:58 | 150 | 50.7% | 39.8% | 7.5% | 1.48% | 0.36% | 0.13% | | 5.3 | 81% | |
| 5B | 1:54 | 150 | 39.7% | 46.2% | 11.1% | 2.35% | 0.39% | 0.17% | 0.14% | 4.2 | 77% | |
| 5C | 3:03 | 150 | 32.9% | 49.1% | 13.9% | 3.20% | 0.65% | 0.29% | | 3.5 | 73% | |
| 5D | 4:13 | 150 | 29.1% | 50.2% | 15.8% | 3.88% | 0.81% | 0.25% | | 3.2 | 71% | |

TABLE II

Summary of Examples 6-9.

| Example | Calcination | | Composition | | | | | | | Dimer/ Trimer | Dimer Yield | Calc. Viscosity |
|---|---|---|---|---|---|---|---|---|---|---|---|---|
| | Time | Temp (° C.) | $C_{12}$ | $C_{24}$ | $C_{36}$ | $C_{48}$ | $C_{60}$ | $C_{72}$ | $C_{84}$ | | | |
| 6A | 0:15 | N/A | 47.8% | 39.7% | 9.1% | 2.45% | 0.72% | 0.28% | | 4.4 | 76% | 2.91 |
| 6B | 0:30 | N/A | 42.9% | 43.0% | 10.5% | 2.65% | 0.59% | 0.33% | | 4.1 | 75% | 2.98 |
| 6C | 1:00 | N/A | 38.7% | 45.4% | 11.9% | 3.00% | 0.71% | 0.27% | | 3.8 | 74% | 2.99 |
| 6D | 2:00 | N/A | 34.9% | 47.5% | 13.2% | 3.25% | 0.78% | 0.33% | | 3.6 | 73% | 3.01 |
| 7A | 0:15 | 100 | 48.7% | 41.0% | 8.1% | 1.68% | 0.42% | 0.12% | | 5.1 | 80% | 2.80 |
| 7B | 0:30 | 100 | 41.8% | 45.0% | 10.3% | 2.22% | 0.53% | 0.12% | | 4.4 | 77% | 2.89 |
| 7C | 1:00 | 100 | 32.9% | 48.9% | 13.9% | 3.25% | 0.73% | 0.35% | | 3.5 | 73% | 2.99 |
| 7D | 2:00 | 100 | 25.4% | 50.6% | 18.0% | 4.65% | 1.08% | 0.28% | | 2.8 | 68% | 3.14 |
| 8A | 0:15 | 200 | 59.5% | 34.3% | 4.9% | 0.76% | 0.24% | 0.26% | | 6.9 | 85% | 2.69 |
| 8B | 0:30 | 200 | 50.6% | 40.4% | 7.3% | 1.46% | 0.31% | 0.03% | | 5.5 | 82% | 2.71 |
| 8C | 1:00 | 200 | 40.1% | 46.2% | 10.7% | 2.21% | 0.44% | 0.34% | | 4.3 | 77% | 2.89 |
| 8D | 2:00 | 200 | 30.3% | 50.1% | 14.9% | 3.51% | 0.81% | 0.40% | | 3.4 | 72% | 3.04 |
| 9A | 0:15 | 300 | 49.9% | 39.4% | 8.3% | 1.83% | 0.42% | 0.13% | | 4.7 | 79% | 2.89 |
| 9B | 0:30 | 300 | 41.5% | 44.1% | 11.0% | 2.59% | 0.64% | 0.21% | | 4.0 | 75% | 2.95 |
| 9C | 1:00 | 300 | 33.6% | 47.5% | 14.3% | 3.51% | 0.81% | 0.26% | | 3.3 | 72% | 3.04 |
| 9D | 2:00 | 300 | 25.3% | 49.2% | 18.7% | 5.17% | 1.33% | 0.29% | | 2.6 | 66% | 3.21 |

Examples 10-11

Polyalphaolefin Properties Resulting from the Oligomerization of 1-dodecene with Sulfated Alumina Example 10 was produced as described above for Example 5. After filtration to remove the sulfated alumina, the oligomer product of Example 10 was subjected to standard distillation conditions capable of separating 1-dodecene from the oligomer product, and then the oligomer product was hydrogenated. Example 11 is a comparative commercial 2.5 cSt PAO product produced from the oligomerization of 1-dodecene using a $BF_3$-based catalyst system. Table III compares the properties of Examples 10-11.

Unexpectedly, the product of Example 10 had higher molecular weight (as reflected by the higher viscosity at 100° C.), than that of Example 11, but with a beneficial combination of a lower viscosity at −40° C. and a higher viscosity index.

TABLE III

Examples 10-11.

| | Example 10 | Example 11 |
|---|---|---|
| Viscosity @ 100° C. (cSt) | 3.2 | 2.4 |
| Viscosity @ 40° C. (cSt) | 12.7 | 8.3 |
| Viscosity @ −40° C. (cSt) | 1445 | 1811 |
| Viscosity Index | 114 | 109 |
| Bromine Index | 93 | ~50 |

Examples 12-14

Oligomerization of 1-dodecene with Different Chemically-treated Solid Oxides

In a drybox under an $N_2$ atmosphere, a 30 mL glass vial vessel was charged with a chemically-treated solid oxide and 10 mL of pre-dried and degassed 1-dodecene. The glass vial was sealed and the mixture was stirred at 25° C., for a set period of time. The liquid phase was separated by filtration. A sample of the liquid phase was then analyzed by gas chromatography to determine composition of the reaction mixture. Table IV provides the reaction information for Examples 12-14 and the compositional make-up of the liquid samples. Example 12 used sulfated alumina (S-A), Example 13 used fluorided silica-coated alumina (F-SCA), and Example 14 used fluorided/chlorided silica-coated alumina (F/Cl-SCA).

As shown in Table IV, at a reaction temperature of 25° C., Examples 13-14 (fluorided silica-coated alumina, fluorided/chlorided silica-coated alumina) had significantly higher monomer conversions than Example 12 (sulfated alumina), resulting in the production of from 30% to over 100% more oligomer product from 1-dodecene. Examples 13-14 also had surprisingly high selectivity to the dimer, with ratios of dimer:trimer ranging from 2.2:1 to 2.5:1.

Examples 15-17

Oligomerization of 1-hexene with Different Chemically-treated Solid Oxides

In a drybox under an $N_2$ atmosphere, a 30 mL glass vial vessel was charged with a chemically-treated solid oxide and 15 mL of pre-dried and degassed 1-hexene. The glass vial was sealed and the mixture was stirred at 51° C. for 1 hour. The liquid phase was separated by filtration and the unreacted 1-hexene was then removed by rotoevaporation at room temperature. A sample of the rotoevaporated liquid phase was then analyzed by gas chromatography to determine the composition of the reaction mixture. Table V provides reaction information for Examples 15-17 and the compositional make-up of the product samples. Example 15 used sulfated alumina (S-A), Example 16 used fluorided silica-coated alumina (F-SCA), and Example 17 used fluorided/chlorided silica-coated alumina (F/Cl-SCA).

As shown in Table V, at a reaction temperature of 51° C., Examples 16-17 (fluorided silica-coated alumina, fluorided/chlorided silica-coated alumina) had significantly higher monomer conversions than Example 15 (sulfated alumina), resulting in the production of 20% more oligomer product from 1-hexene. Examples 15-16 also had surprisingly high selectivity to the trimer, with ratios of trimer:dimer ranging from 1.05:1 to 1.8:1, and ratios of trimer:tetramer ranging from 4.2:1 to 7:1.

Examples 18-21

Oligomerization of Propylene with Different Chemically-treated Solid Oxides

A 4-L steel autoclave reactor was loaded with 1 g of the catalyst under a purging stream of $N_2$. The reactor was sealed and then charged with 2.7 liters of propylene. The reactor was brought to the reaction temperature and stirred for 1 hour. The reactor temperature was then lowered to 40° C., the reactor was vented and then opened, and the liquid product was collected. Product samples were analyzed by gas chromatography to determine the composition of the reaction mixture. Table VI provides reaction information for Examples 18-21 and the compositional make-up of the product samples. Example 18 used sulfated alumina (S-A), and Examples 19-21 used fluorided silica-coated alumina (F-SCA).

As shown in Table VI, Examples 19-21 (fluorided silica-coated alumina) had significantly higher monomer conversions than Example 18 (sulfated alumina), resulting in the production of from 30% to 75% more oligomer product from propylene. Examples 19-21 also had unexpectedly high trimer/tetramer yield, with about 82-83 wt. % of the oligomer product (excluding residual monomer) being $C_9$ or $C_{12}$. Moreover, the oligomer products of Examples 19-21 contained over 40 wt. % trimer, and a ratio of trimer:tetramer ranging from 1.2:1 to 1.3:1.

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1. A process comprising:

(i) introducing a monomer comprising a $C_3$ to $C_{30}$ olefin and a chemically-treated solid oxide into a reaction zone; and (ii) oligomerizing the monomer to form an oligomer product in the reaction zone.

Embodiment 2. The process defined in embodiment 1, wherein the chemically-treated solid oxide comprises a solid oxide treated with an electron-withdrawing anion, e.g., any solid oxide and any electron-withdrawing anion disclosed herein.

Embodiment 3. The process defined in embodiment 2, wherein (a) the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof, and (b) the electron-withdrawing anion comprises sulfate, bisulfate, fluoride, chloride, bromide,

TABLE IV

Summary of Examples 12-14.

| Example | Catalyst Type | Catalyst (mg) | 1-dodecene (mL) | Temperature (° C.) | Reaction time (hr) | 1-dodecene conversion (wt. %) | Product Composition Dimer (wt. %) | Trimer (wt. %) |
|---|---|---|---|---|---|---|---|---|
| 12 | S-A | 410 | 10 | 25 | 2 | 14.4 | 78.3 | 21.7 |
| 13 | F-SCA | 410 | 10 | 25 | 2 | 18.9 | 69.1 | 30.9 |
| 14 | F/Cl-SCA | 425 | 10 | 25 | 2.2 | 30.1 | 71.3 | 28.7 |

TABLE V

Summary of Examples 15-17.

| Example | Catalyst Type | Catalyst (mg) | 1-hexene (g) | Product (g) | 1-hexene conversion (wt. %) | Dimer (wt. %) | Trimer (wt. %) | Tetramer (wt. %) |
|---|---|---|---|---|---|---|---|---|
| 15 | S-A | 326 | 10.17 | 4.22 | 41.4 | 53.6 | 41.0 | 5.4 |
| 16 | F-SCA | 330 | 10.17 | 5.11 | 50.2 | 31.5 | 55.4 | 13.1 |
| 17 | F/Cl-SCA | 331 | 10.17 | 5.08 | 49.9 | 45.1 | 48.2 | 6.8 |

TABLE VI

Summary of Examples 18-21.

| Example | Catalyst Type | Catalyst (g) | Reactor pressure (psig) | Temperature (° C.) | Product (g) | Product Composition (wt. %) | | | | | | |
|---|---|---|---|---|---|---|---|---|---|---|---|---|
| | | | | | | $C_6$ | $C_9$ | $C_{12}$ | $C_{15}$ | $C_{18}$ | $C_{21}$ | $C_{24}$ |
| 18 | S-A | 1 | 440 | 70 | 23 | 3.5 | 48.3 | 34.3 | 9.3 | 3.3 | 1.0 | 0.4 |
| 19 | F-SCA | 1 | 448 | 70 | 30 | 3.2 | 46.1 | 37.0 | 9.6 | 2.9 | 0.9 | 0.2 |
| 20 | F-SCA | 1 | 445 | 70 | 31 | 2.5 | 44.6 | 38.1 | 10.3 | 3.3 | 0.9 | 0.3 |
| 21 | F-SCA | 1 | 500 | 80 | 40 | 3.0 | 47.1 | 35.7 | 9.9 | 3.1 | 0.9 | 0.2 | iodide, fluorosulfate, fluoroborate, phosphate, fluorophosphate, trifluoroacetate, triflate, fluorozirconate, fluorotitanate, phospho-tungstate, or any combination thereof.

Embodiment 4. The process defined in embodiment 2 or 3, wherein the solid oxide comprises silica, alumina, silica-alumina, silica-coated alumina, or a mixture thereof.

Embodiment 5. The process defined in embodiment 2 or 3, wherein the solid oxide comprises silica-coated alumina.

Embodiment 6. The process defined in any one of embodiments 2-5, wherein the electron-withdrawing anion comprises sulfate, fluoride, chloride, or any combination thereof.

Embodiment 7. The process defined in any one of embodiments 2-6, wherein the electron-withdrawing anion comprises sulfate.

Embodiment 8. The process defined in any one of embodiments 2-6, wherein the electron-withdrawing anion comprises fluoride, chloride, or both.

Embodiment 9. The process defined in embodiment 1 or 2, wherein the chemically-treated solid oxide comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Embodiment 10. The process defined in embodiment 1 or 2, wherein the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

Embodiment 11. The process defined in embodiment 1 or 2, wherein the chemically-treated solid oxide comprises fluorided silica-coated alumina.

Embodiment 12. The process defined in embodiment 1 or 2, wherein the chemically-treated solid oxide comprises fluorided-chlorided silica-coated alumina.

Embodiment 13. The process defined in any one of embodiments 2-12, wherein the weight percentage of the electron-withdrawing anion, based on the weight of the chemically-treated solid oxide, is any suitable amount or in any range of weight percentages disclosed herein, e.g., from 1 to 20 wt. %, from 2 to 15 wt. %, or from 3 to 12 wt. %.

Embodiment 14. The process defined in any one of the preceding embodiments, wherein the chemically-treated solid oxide comprises silica-coated alumina comprising silica in any suitable amount or in any range of weight percentages disclosed herein, e.g., from 10 to 80 wt. % silica, from 25 to 48 wt. % silica, or from 20 to 45 wt. % silica, based on the weight of the silica-coated alumina.

Embodiment 15. The process defined in any one of the preceding embodiments, wherein the oligomerizing step is conducted in the substantially absence of organoaluminum compounds, metallocene compounds, or combinations thereof.

Embodiment 16. The process defined in any one of embodiments 1-15, wherein the monomer comprises any suitable amount of the $C_3$ to $C_{30}$ olefin or an amount of the $C_3$ to $C_{30}$ olefin in any range disclosed herein, e.g., at least 50 wt. %, at least 70 wt. %, at least 80 wt. %, at least 90 wt. %, at least 95 wt. %, from 50 to 100 wt. %, from 80 to 100 wt. %, or from 80 to 98 wt. %.

Embodiment 17. The process defined in any one of embodiments 1-16, wherein the monomer comprises a $C_3$ to $C_5$ olefin, a $C_6$ to $C_{18}$ olefin, or a $C_8$ to $C_{12}$ olefin.

Embodiment 18. The process defined in any one of embodiments 1-16, wherein the monomer comprises a $C_3$ to $C_{30}$ alpha olefin, a $C_3$ to $C_5$ alpha olefin, a $C_6$ to $C_{18}$ alpha olefin, or a $C_8$ to $C_{12}$ alpha olefin.

Embodiment 19. The process defined in any one of embodiments 1-16, wherein the monomer comprises a $C_3$ to $C_{30}$ normal alpha olefin, a $C_3$ to $C_5$ normal alpha olefin, a $C_6$ to $C_{18}$ normal alpha olefin, or a $C_8$ to $C_{12}$ normal alpha olefin.

Embodiment 20. The process defined in any one of embodiments 1-16, wherein the monomer comprises propylene; alternatively, 1-butene; or alternatively, 1-pentene.

Embodiment 21. The process defined in any one of embodiments 1-16, wherein the monomer comprises 1-hexene, 1-octene, 1-decene, 1-dodecene, 1-tetradecene, 1-hexadecene, or any combination thereof; alternatively, 1-octene, 1-decene, 1-dodecene, or any combination thereof; alternatively, 1-hexene; alternatively, 1-octene; alternatively, 1-decene, alternatively, 1-dodecene; alternatively, 1-tetradecene; or alternatively, 1-hexadecene.

Embodiment 22. The process defined in any one of embodiments 1-21, wherein the oligomer product is formed at any suitable oligomerization temperature or at an oligomerization temperature in any range disclosed herein, e.g., from 0° C. to 250° C., from 15° C. to 225° C., or from 20° C. to 180° C.

Embodiment 23. The process defined in any one of embodiments 1-22, wherein the reaction zone comprises any suitable reactor or any reactor disclosed herein, e.g., a fixed bed reactor, a stirred tank reactor, a plug flow reactor, a tubular reactor, or any combination thereof.

Embodiment 24. The process defined in any one of embodiments 1-23, wherein a weight ratio of the monomer (comprising the $C_3$ to $C_{30}$ olefin or any other olefin described herein) to the chemically-treated solid oxide is in any suitable range or in any range of weight ratios disclosed herein, e.g., from 1:1 to 1000:1, or from 2:1 to 100:1.

Embodiment 25. The process defined in any one of embodiments 1-24, wherein the process is conducted in a fixed bed reactor, and wherein the monomer (comprising the $C_3$ to $C_{30}$ olefin or any other olefin described herein) and the chemically-treated solid oxide are contacted at any suitable WHSV or a WHSV in any range disclosed herein, e.g., from 0.05 to 5, from 0.1 to 3, or from 0.5 to 2.5.

Embodiment 26. The process defined in any one of embodiments 1-25, wherein a conversion (or single pass conversion) of the monomer (comprising the $C_3$ to $C_{30}$ olefin or any other olefin described herein) to the oligomer product is any suitable conversion (or single pass conversion) or in any range of conversions (or single pass conversions) disclosed herein, e.g., from 10 to 95 wt. %, from 20 to 90 wt. %, from 30 to 85 wt. %, from 40 to 80 wt. %, from 40 to 75 wt. %, or from 15 to 75 wt. %.

Embodiment 27. The process defined in any one of embodiments 1-26, wherein the monomer comprises propylene, and wherein the oligomer product comprises at least 40 wt. % trimers and/or a weight ratio of trimers to tetramers in the oligomer product is greater than 1:1, e.g., from 1.05:1 to 1.6:1.

Embodiment 28. The process defined in any one of embodiments 1-26, wherein the monomer comprises 1-butene, 1-pentene, 1-hexene, or any combination thereof, and wherein the oligomer product comprises at least 40 wt.

% trimers and/or a weight ratio of trimers to dimers in the oligomer product is greater than 1:1, e.g., from 1.02:1 to 2:1.

Embodiment 29. The process defined in any one of embodiments 1-26, wherein the monomer comprises any $C_8$ to $C_{12}$ olefin described herein (e.g., 1-octene, 1-decene, 1-dodecene, or any combination thereof), and wherein the oligomer product comprises at least 30 wt. % dimers and/or a weight ratio of dimers to trimers in the oligomer product is greater than 0.5:1, e.g., greater than 1:1, from 0.5:1 to 6:1, or from 2:1 to 8:1.

Embodiment 30. The process defined in any one of embodiments 1-26, wherein the monomer comprises 1-dodecene, and wherein the oligomer product comprises from 30 to 98 wt. % dimers and/or a weight ratio of dimers to trimers in the oligomer product is from 2:1 to 6:1.

Embodiment 31. The process defined in any one of embodiments 1-26, wherein the monomer comprises 1-dodecene, and wherein the oligomer product comprises from 55 to 95 wt. % dimers and/or a weight ratio of dimers to trimers in the oligomer product is from 1.5:1 to 8:1.

Embodiment 32. The process defined in any one of embodiments 1-31, wherein the chemically-treated solid oxide comprises fluorided silica-coated alumina, and wherein a conversion (or single pass conversion) of the monomer (comprising the $C_3$ to $C_{30}$ olefin or any other olefin described herein) to the oligomer product is greater than that of a comparable process using sulfated alumina (instead of fluorided silica-coated alumina), under the same oligomerization conditions.

Embodiment 33. The process defined in any one of embodiments 1-31, wherein the chemically-treated solid oxide comprises fluorided-chlorided silica-coated alumina, and wherein a conversion (or single pass conversion) of the monomer (comprising the $C_3$ to $C_{30}$ olefin or any other olefin described herein) to the oligomer product is greater than that of a comparable process using sulfated alumina (instead of fluorided-chlorided silica-coated alumina), under the same oligomerization conditions.

Embodiment 34. The process defined in any one of embodiments 1-33, wherein the process further comprises a step of removing a reactor effluent from the reaction zone and separating at least a portion of the chemically-treated solid oxide from the reactor effluent.

Embodiment 35. The process defined in embodiment 34, wherein the removing step is performed using any suitable technique or any technique disclosed herein, e.g., filtration, evaporation, or distillation, as well as combinations thereof.

Embodiment 36. The process defined in any one of embodiments 1-35, wherein the process further comprises a step of removing at least a portion of the monomer from the reactor effluent.

Embodiment 37. The process defined in any one of embodiments 1-36, wherein the process further comprises a step of isolating one or more fractions comprising all or a portion of the oligomer product.

Embodiment 38. The process defined of embodiment 37, wherein the isolating step is performed using any suitable technique or any technique disclosed herein, e.g., filtration, evaporation, or distillation, as well as combinations thereof.

Embodiment 39. The process defined in any one of embodiments 37-38, wherein the process further comprises a step of hydrogenating at least one of the one or more fractions comprising all or a portion of the oligomer product using any suitable technique, or any technique disclosed herein, to form a polyalphaolefin.

Embodiment 40. An oligomer product (or fraction comprising all or a portion of the oligomer product) produced by the process defined in any one of embodiments 1-38.

Embodiment 41. A polyalphaolefin produced by the process defined in embodiment 39.

Embodiment 42. A composition comprising the oligomer product (or fraction comprising all or a portion of the oligomer product) defined in embodiment 40 or the polyalphaolefin defined in embodiment 41.

Embodiment 43. A base oil or lubricant composition comprising the oligomer product (or fraction comprising all or a portion of the oligomer product) defined in embodiment 40 or the polyalphaolefin defined in embodiment 41.

Embodiment 44. A polyalphaolefin comprising (at least 80 wt. %) hydrogenated oligomers of a $C_6$ to $C_{12}$ olefin (or any other $C_6$ to $C_{12}$ olefin described herein), wherein the polyalphaolefin has a viscosity index greater than or equal to 110 and a kinematic viscosity at $-40°$ C. of less than or equal to 1750 cSt.

Embodiment 45. The polyalphaolefin defined in embodiment 44, wherein the polyalphaolefin further comprises hydrogenated dimers and trimers, and having any weight ratio of hydrogenated dimers:trimers greater than or equal to 2:1 described herein, e.g., from 2:1 to 6:1.

Embodiment 46. A polyalphaolefin comprising at least 30 wt. % $C_{24}$ saturated hydrocarbons, wherein the polyalphaolefin has a viscosity index greater than or equal to 110 and a kinematic viscosity at $-40°$ C. of less than or equal to 1750 cSt.

Embodiment 47. The process defined in embodiment 46, wherein the polyalphaolefin further comprises $C_{36}$ saturated hydrocarbons, and a weight ratio of $C_{24}:C_{36}$ saturated hydrocarbons is greater than or equal to 2:1, e.g., from 2:1 to 6:1.

Embodiment 48. The polyalphaolefin defined in any one of embodiments 44-47, wherein the polyalphaolefin has a viscosity index in a range from 110 to 125.

Embodiment 49. The polyalphaolefin defined in any one of embodiments 44-48, wherein the polyalphaolefin has a kinematic viscosity at $-40°$ C. in a range from 1300 to 1700 cSt.

Embodiment 50. The polyalphaolefin defined in any one of embodiments 44-49, wherein the polyalphaolefin has a kinematic viscosity at 40° C. in a range from 9 to 15 cSt.

Embodiment 51. The polyalphaolefin defined in any one of embodiments 44-50, wherein the polyalphaolefin has a kinematic viscosity at 100° C. in a range from 1.8 to 12 cSt.

We claim:
1. A process comprising:
   (i) introducing a monomer comprising a $C_3$ to $C_{30}$ olefin and a catalyst consisting of a chemically-treated solid oxide into a reaction zone, the chemically-treated solid oxide comprising a silica-coated alumina treated with an electron-withdrawing anion; and
   (ii) oligomerizing the monomer to form an oligomer product in the reaction zone;
   wherein the oligomer product comprises at least 30 wt % dimers.

2. The process of claim 1, wherein the chemically-treated solid oxide comprises fluorided silica-coated alumina.

3. The process of claim 2, wherein a conversion of the monomer to the oligomer product is greater than that of a comparable process using sulfated alumina, under the same oligomerization conditions.

4. The process of claim 1, wherein the chemically-treated solid oxide comprises fluorided-chlorided silica-coated alumina.

5. The process of claim 4, wherein a conversion of the monomer to the oligomer product is greater than that of a comparable process using sulfated alumina, under the same oligomerization conditions.

6. The process of claim 1, wherein:
the silica-coated alumina comprises from 20 to 45 wt % silica, based on the weight of the silica-coated alumina; and
the electron-withdrawing anion comprises sulfate, fluoride, chloride, or any combination thereof.

7. The process of claim 1, wherein the monomer comprises at least 75 wt % $C_3$ to $C_{18}$ alpha olefins.

8. The process of claim 1, wherein the monomer comprises propylene, 1-butene, 1-pentene, 1-hexene, 1-octene, 1-decene, 1-dodecene, 1-tetradecene, 1-hexadecene, or any combination thereof.

9. The process of claim 1, wherein the monomer comprises propylene, and wherein the oligomer product comprises at least 40 wt % trimers and/or a weight ratio of trimers to tetramers in the oligomer product is greater than 1:1.

10. The process of claim 1, wherein the monomer comprises 1-butene, 1-pentene, 1-hexene, or any combination thereof and wherein the oligomer product comprises at least 40 wt % trimers and/or a weight ratio of trimers to dimers in the oligomer product is greater than 1:1.

11. The process of claim 1, wherein the monomer comprises 1-octene, 1-decene, 1-dodecene, or any combination thereof, and wherein a weight ratio of dimers to trimers in the oligomer product is greater than 1:1.

12. A process comprising:
(i) introducing a monomer comprising a $C_3$ to $C_8$ olefin and a catalyst consisting of a chemically-treated solid oxide into a reaction zone, the chemically-treated solid oxide comprising a silica-coated alumina treated with an electron-withdrawing anion; and
(ii) oligomerizing the monomer to form an oligomer product in the reaction zone;
wherein the oligomer product comprises at least 30 wt % trimers.

13. The process of claim 12, wherein the electron-withdrawing anion comprises sulfate, fluoride, chloride, or any combination thereof.

14. The process of claim 12, wherein the monomer comprises propylene, and wherein a weight ratio of trimers to tetramers in the oligomer product is in a range from 1.05:1 to 1.6:1.

15. The process of claim 14, wherein:
the oligomer product comprises from 35 to 60 wt % trimers; and
the chemically-treated solid oxide comprises fluorided silica-coated alumina and/or fluorided-chlorided silica-coated alumina.

16. The process of claim 12, wherein the monomer comprises 1-hexene, and wherein a weight ratio of trimers to dimers in the oligomer product is in a range from 1.02:1 to 2:1.

17. The process of claim 16, wherein:
the oligomer product comprises from 35 to 65 wt % trimers; and
the chemically-treated solid oxide comprises fluorided silica-coated alumina and/or fluorided-chlorided silica-coated alumina.

* * * * *